United States Patent
Isola et al.

(10) Patent No.: US 10,821,300 B2
(45) Date of Patent: Nov. 3, 2020

(54) PLANNING SYSTEM FOR ADAPTIVE RADIATION THERAPY

(71) Applicant: KONINKLIJKE PHILIPS N.V., Eindhoven (NL)

(72) Inventors: Alfonso Agatino Isola, Eindhoven (NL); Rolf Jürgen Weese, Norderstedt (DE); Christoph Neukirchen, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 235 days.

(21) Appl. No.: 16/120,482

(22) Filed: Sep. 4, 2018

(65) Prior Publication Data

US 2019/0054315 A1 Feb. 21, 2019

Related U.S. Application Data

(63) Continuation-in-part of application No. PCT/EP2018/060194, filed on Apr. 20, 2018.

(30) Foreign Application Priority Data

Apr. 21, 2017 (EP) .................................... 17167452

(51) Int. Cl.
*A61N 5/10* (2006.01)

(52) U.S. Cl.
CPC ......... *A61N 5/1031* (2013.01); *A61N 5/1038* (2013.01); *A61N 5/1039* (2013.01); *A61N 5/1081* (2013.01)

(58) Field of Classification Search
CPC ........ A61N 5/00; A61N 5/103; A61N 5/1031; A61N 5/1038; A61N 5/1039; A61N 5/1081

(Continued)

(56) References Cited

U.S. PATENT DOCUMENTS

2008/0071131 A1 3/2008 Rietzel
2010/0046706 A1 2/2010 Moreau
(Continued)

FOREIGN PATENT DOCUMENTS

WO 2015083035 6/2015
WO 2015150575 10/2015
(Continued)

OTHER PUBLICATIONS

Sotiras, et al., "Deformable Medical Image Registration: A Survey", IEEE Transactions on Medical Imaging 2013, 32 (7), 1153-1190.
(Continued)

*Primary Examiner* — John P Lacyk

(57) ABSTRACT

In planning of radiation therapy treatment of at least one structure in a region of a patient body, a first treatment plan is generated on the basis of a planning image of the body region and on the basis of dose objectives. A further image of the body region of the patient body is received, and a transformation is determined for generating an adapted treatment plan from the first treatment plan and/or for generating an adapted dose distribution from the dose distribution corresponding to the first treatment plan on the basis of the further image and determines an adapted treatment plan on the basis of the transformation and/or the adapted dose distribution. The transformation on the basis of the dose objectives. In adapting the dose distribution, an efficient iterative dosimetric patient setup optimization may be employed to reduce the dose computations.

20 Claims, 10 Drawing Sheets

(58) Field of Classification Search
 USPC .......................................................... 600/1–8
 See application file for complete search history.

(56) References Cited

U.S. PATENT DOCUMENTS

| | | |
|---|---|---|
| 2010/0232572 A1 | 9/2010 | Nord |
| 2013/0324784 A1 | 12/2013 | Fredriksson |
| 2013/0326405 A1 | 12/2013 | Nord |
| 2014/0019440 A1 | 1/2014 | Kim |

FOREIGN PATENT DOCUMENTS

| | | |
|---|---|---|
| WO | 2016/023786 | 2/2016 |
| WO | 2016046683 | 3/2016 |

OTHER PUBLICATIONS

Yelin Suh, et al., "IMRT Treatment Planning on 4D Geometries for the Era of Dynamic MLC Tracking", Technology in Cancer Research and Treatment, vol. 13, No. 6, Dec. 1, 2014.

Michael Unser, "Splines: A perfect fit for signal and image processing", IEEE Sig. Proc. Mag., vol. 16, pp. 22-38, 1999.

| Plans | Dose Statistics | Prostate | Bladder | Rectum | Left femur | Right femur | External |
|---|---|---|---|---|---|---|---|
| Original | Mean (±STD) | 79.95 (±0.56) | 15.28 (±17.54) | 19.49 (±22.30) | 12.70 (±10.61) | 12.46 (±10.62) | 7.75 (±14.37) |
| Shifted resim-CT | Mean (±STD) | 73.61 (±11.91) | 18.64 (±22.24) | 14.08 (±15.82) | 8.32 (±8.02) | 9.71 (±8.99) | 7.88 (±14.56) |
| DPSO | Mean (±STD) | 79.90 (±0.57) | 15.25 (±17.52) | 19.45 (±22.25) | 12.67 (±10.58) | 12.41 (±10.59) | 7.76 (±14.38) |

FIG. 7

PLANNING SYSTEM FOR ADAPTIVE RADIATION THERAPY

PRIORITY

This application is a continuation-in-part of Application Serial No. PCT/EP2018/060194, filed Apr. 20, 2018, which claims priority to Application Serial No. EP 17167452.6, filed Apr. 21, 2017, both which are incorporated herein by reference in their entireties.

FIELD OF THE INVENTION

The following generally relates to adaptive radiation therapy. More specifically, the following is related to a system and to a method for planning a radiation therapy treatment of at least one structure in a region of a patient body. Further, the following is related to a computer program for performing the method.

BACKGROUND

In external beam radiation therapy, ionizing radiation is applied to target structures, such as tumors, within patients' bodies in order to control growth of or kill cancer cells. In more advanced types of radiation therapy, precise doses of radiation are applied to regions of the patient's body. In this respect, it is typically the goal to deliver a sufficiently high radiation dose to the target structure and to spare sensitive structures, which are usually also referred to as organs at risk (OAR), in the vicinity of the target structure as far as possible.

The treatment parameters for controlling the irradiation of the patient are defined in a treatment plan, which particularly specifies the intensity and shape of the radiation beam for irradiating the patient during the treatment. The treatment plan may be determined in an inverse planning procedure on the basis of a planning image of the relevant region of the patient body. In this procedure, treatment goals may be specified which comprise requirements for the radiation dose delivered to the target structure and the OARs during the treatment. Then, an optimization process is carried out to find a treatment plan which results in a distribution of the accumulated dose delivered to the patient, which fulfills the treatment goals with respect to the anatomical structure of the relevant region of the patient body as shown in the planning image. The optimization process usually comprises an operator-guided iterative procedure, in which a planner repeatedly changes parameters until a treatment plan corresponding to an acceptable dose distribution is found and approved.

Since this planning procedure is quite complex and time-consuming it is usually carried out some time (up to several days) in advance of the treatment. However, this means that the anatomical configuration of the relevant region of the body changes between the acquisition of the planning image and the delivery of the treatment. As a result, the generated treatment plan may no longer be accurate and the shifted and/or deformed target structure may receive less radiation and the shifted and/or deformed OARs may receive more radiation than intended, when the treatment is delivered on the basis of the initial treatment plan.

Therefore, the initial treatment plan may be adapted before the delivery of the treatment on the basis of a new image of the relevant region of the patient body. This image may effectively be acquired in the treatment room and, therefore, it is also referred to as in-room image herein below. In the process of adapting the treatment plan, an adapted dose distribution may be determined in accordance with the changed patient anatomy and the treatment plan may be modified to deliver the adapted dose distribution. The adapted dose distribution is determined on the basis of a transformation of the dose distribution corresponding to the original treatment plan. In order to limit the complexity of the plan adaptation, a rigid transformation may be used in order to approximately adapt the plan to the changed anatomy.

The transformation may be determined on the basis of a comparison of the anatomical configurations of the relevant region of the patient body as shown in the planning image and in the in-room image. However, it has been found that this approach can result in a modified treatment plan which does not allow for fulfilling the treatment objectives sufficient accurately.

BRIEF SUMMARY

Some embodiments disclosed herein allow for an improved adaptation of an initial treatment plan on the basis of an in-room image such that the treatment objectives are more reliable fulfilled using the adapted treatment plan.

In accordance with a first aspect, a system is provided for planning a radiation therapy treatment of at least one structure, which may be a target structure of the treatment, in a region of a patient body. The system comprises a planning unit configured to (i) obtain a first treatment plan generated on the basis of a planning image of the region of the patient body and on the basis of dose objectives with respect to the region of the patient body, the first treatment plan corresponding to a first dose distribution in the region of the patient body, (ii) receive a further image of the region of the patient body, (iii) determine a transformation for generating an adapted treatment plan and/or for generating an adapted dose distribution from the first dose distribution on the basis of the further image, and (iv) determine an adapted treatment plan for controlling the radiation therapy treatment on the basis of the transformation and/or the adapted dose distribution. Further, the planning unit is configured to determine the transformation on the basis of the dose objectives.

Since the transformation is determined on the basis of the dose objectives rather than on the basis of the comparison of anatomical features shown in the planning image and the further image, the adaptation of the treatment plan can be improved and the treatment objectives can more reliable be fulfilled on the basis of the adapted treatment plan. The transformation may particularly be rigid transformation, i.e. a transformation consisting of a rotation and/or a translation. Hereby, the complexity of the adaptation procedure can be limited.

The generated transformation may be used to directly determine the adapted treatment plan from the first treatment plan. In particular, directions of the radiation beam specified in the first treatment plan may be rotated on the basis of the transformation and/or positions of the radiation source specified in the first treatment plan may be displacement on the basis of the transformation in order to determine the adapted treatment plan.

In a possible further approach, an adapted dose distribution may be determined from the first dose distribution using the transformation, and the adapted treatment plan is generated on the basis of the adapted dose distribution. In particular, the adapted treatment plan may be generated such that the adapted dose distribution is achieved when the radiation therapy treatment is delivered on the basis of the adapted treatment plan.

In accordance with another aspect in some embodiments, the first treatment plan is generated on the basis of a first delineation of the at least one structure determined on the basis of the planning image and wherein the planning unit is configured to generate the transformation on the basis of a second delineation of the at least one structure determined on the basis of the further image. In order to generate the second delineation, the at least one structure may be newly delineated in the further image. In a preferred alternative implementation, the planning unit is configured to generate the second delineation from the first delineation using an image transformation, the image transformation being determined on the basis of an image registration procedure between the further image and the planning image. The transform may particularly be a non-rigid transform in order to allow for accurately determining the second delineation.

With respect to the transformation used for adapting the treatment plan, one embodiment includes that the planning unit is configured to determine the transformation by optimizing an objective functional generated on the basis of the dose objectives evaluated for a dose distribution resulting from the first treatment plan and a patient anatomy as represented by a transformed second image and a transformed second delineation of the at least one structure, the objective function being optimized with respect to the transformation for generating the transformed second image and the transformed second delineation. In this manner, it is possible to determine the transformation on the basis of the dose objectives. These dose objectives are particularly taken into account in the determination of the transformation through the form of the objective functional which is determined on the basis of the dose objectives.

In a related embodiment, the planning unit is configured to determine the transformation such that an objective functional $O(T)$ of a transformation $T$ of the form $O(T)=F(d[p_1,T*I_2],T*s_2)$ is at least approximately optimized when the transformation $T$ corresponds to the determined transformation, where $F$ is a functional generated on the basis of the dose objectives, $d$ is a dose distribution in the region of the patient body, $p_1$ is first treatment plan, $I_2$ is the second image, $T*I_2$ is a transform of the second image generated using the transformation $T$, $s_2$ is the second delineation of the target structure and $T*s_2$ is a transform of the second delineation generated based on the transformation $T$.

Moreover, it is possible to generate a plurality of first treatment plans in the initial planning procedure for planning the radiation therapy treatment. These first treatment plans may particularly be generated using different safety margins or for different anatomical configurations of the relevant region of the patient body including the at least one structure to be treated. These different anatomical configurations may be generated by anticipating typical deformations of the relevant body region.

In this respect, one embodiment includes that the planning unit is configured to (i) obtain a plurality of first treatment plans generated on the basis of the dose objectives, (ii) at least approximately optimize the objective functional for each of the first treatment plans and to compare the optima of the objective function determined for the treatment plan, and (iii) determine an adapted treatment for controlling the radiation therapy treatment on the basis of the result of the comparison.

In this embodiment, the optimum of the objective functional serves as a measure for assessing the suitability of the different first treatment plans for delivering the radiation therapy treatment to the changed patient anatomy as shown in the further image. The different first treatment plans may be generated on the basis of different settings of the radiation source delivering the radiation which result in a similar dose distribution, on the basis different anatomical configurations of the region of the patient body including the target structure and/or on the basis of different safety margins for the target structure and/or the OARs on the basis of which the treatment plans have been generated.

In a related embodiment, the planning unit is configured to select one of the first treatment plans on the basis of the comparison and to adapt the treatment on the basis of the transformation determined by optimizing the objective function for the selected treatment plan.

In a further related embodiment, the planning unit is configured to determine a combined treatment plan on the basis of the first treatment plans on the basis of the comparison and to adapt the combined treatment plan on the basis of the transformations determined by optimizing the objective functionals for the treatment plans.

In some further embodiments, the system further comprises an imaging unit for acquiring the further image of the region of the patient body and the planning unit is configured to receive the further image from the imaging unit.

In accordance with a further aspect, some embodiments comprises a method for planning a radiation therapy treatment of at least one structure in a region of a patient body. The method comprises: (i) obtaining a first treatment plan generated on the basis of a planning image of the region of the patient body and on the basis of dose objectives with respect to the region of the patient body, the first treatment plan corresponding to a first dose distribution in the region of the patient body, (ii) receiving a further image of the region of the patient body, (iii) determining a transformation for generating an adapted dose distribution from the first dose distribution on the basis of the further image and the planning image, and (iv) determining an adapted treatment plan for controlling the radiation therapy treatment on the basis of the transformation and/or the adapted dose distribution. The transformation is determined on the basis of the dose objectives.

In a further aspect, some embodiments comprise a computer program product comprising instructions which, when the program is executed by a computer, cause the computer to carry out the method, particularly a computer of the system described above.

In a further aspect, in some embodiments a non-transitory computer-readable medium stores instructions readable and executable by at least one electronic processor to perform a treatment planning method. In the method, a treatment plan is obtained. The treatment plan was generated on the basis of a planning image of a region of a patient body and on the basis of dose objectives with respect to the region of the patient body. The treatment plan corresponds to a dose distribution in the region of the patient body. A further image of the region of the patient body is received. A transformation is determined for generating an adapted treatment plan by at least one adjustment iteration in which the dose distribution is updated for a rigid spatial transform and the rigid spatial transform is updated on the basis of the dose objectives using a partial derivative of the dose objectives with respect to the rigid spatial transform but not using a partial derivative of the dose objectives with respect to the dose distribution. The transformation comprises the rigid spatial transform updated by the last adjustment iteration.

An adapted treatment plan for controlling the radiation therapy treatment is determined on the basis of the transformation.

In a further aspect, in some embodiments a treatment planning device is disclosed, including at least one electronic processor and a non-transitory computer-readable medium storing instructions readable and executable by the at least one electronic processor to perform a treatment planning method. The treatment planning method comprises: obtaining a treatment plan generated on the basis of a planning image of a region of a patient body and on the basis of dose objectives with respect to the region of the patient body, the treatment plan corresponding to a dose distribution in the region of the patient body; receiving a further image of the region of the patient body; updating a rigid spatial transform by performing at least one iteration of an update process that does not including computing a partial derivative of the dose objectives with respect to the dose distribution; and adapting the treatment plan to generate an adapted treatment plan which includes an adjustment by the updated rigid spatial transform of patient position respective to a radiation treatment device.

In a further aspect, in some embodiments a treatment planning method is disclosed. A treatment plan is obtained, which was generated on the basis of a planning image of a region of a patient body and on the basis of dose objectives with respect to the region of the patient body, the treatment plan corresponding to a dose distribution in the region of the patient body. A further image of the region of the patient body is received. A rigid spatial transform is determined for generating at least one of an adapted treatment plan from the treatment plan and an adapted dose distribution from the dose distribution on the basis of the further image and on the basis of the dose objectives. The rigid spatial transform is determined using an iterative process that alternates between updating the dose distribution and updating the rigid spatial transform. The treatment plan is adapted to generate an adapted treatment plan which includes an adjustment by the determined rigid spatial transform of patient position respective to a radiation treatment device. The treatment planning method is suitably performed by at least one electronic processor.

It shall be understood that a preferred embodiment can also be any combination of the above embodiments.

One advantage resides in providing adaptive radiation therapy that employs a rigid transformation that is efficiently computed and straightforward to implement, and which does not require recomputation of beam parameters, and which is determined on the basis of the dose objectives.

Another advantage resides in adapting a radiation therapy plan without the need to acquire additional quality assurance (QA) validation.

Another advantage resides in updating a treatment room set-up during delivery of therapy to a patient without the need to adjust the therapy plan.

Another advantage resides in providing a feasible and fast method of limiting the amount of dose computations required to obtain an optimal patient setup at each radiation therapy (RT) treatment fraction.

Another advantage resides in reducing a computation burden of dose computations by toggling between dose re-computations and dose-based region shifting is applied to achieve the optimal patient setup.

A given embodiment may provide none, one, two, more, or all of the foregoing advantages, and/or may provide other advantages as will become apparent to one of ordinary skill in the art upon reading and understanding the present disclosure.

These and other aspects of the invention will be apparent from and elucidated with reference to the embodiments described hereinafter.

BRIEF DESCRIPTION OF THE DRAWINGS

In the following drawings:

FIGS. 4-10 show treatment planning results using the system of FIG. 1.

DETAILED DESCRIPTION OF EMBODIMENTS

Figure 1:
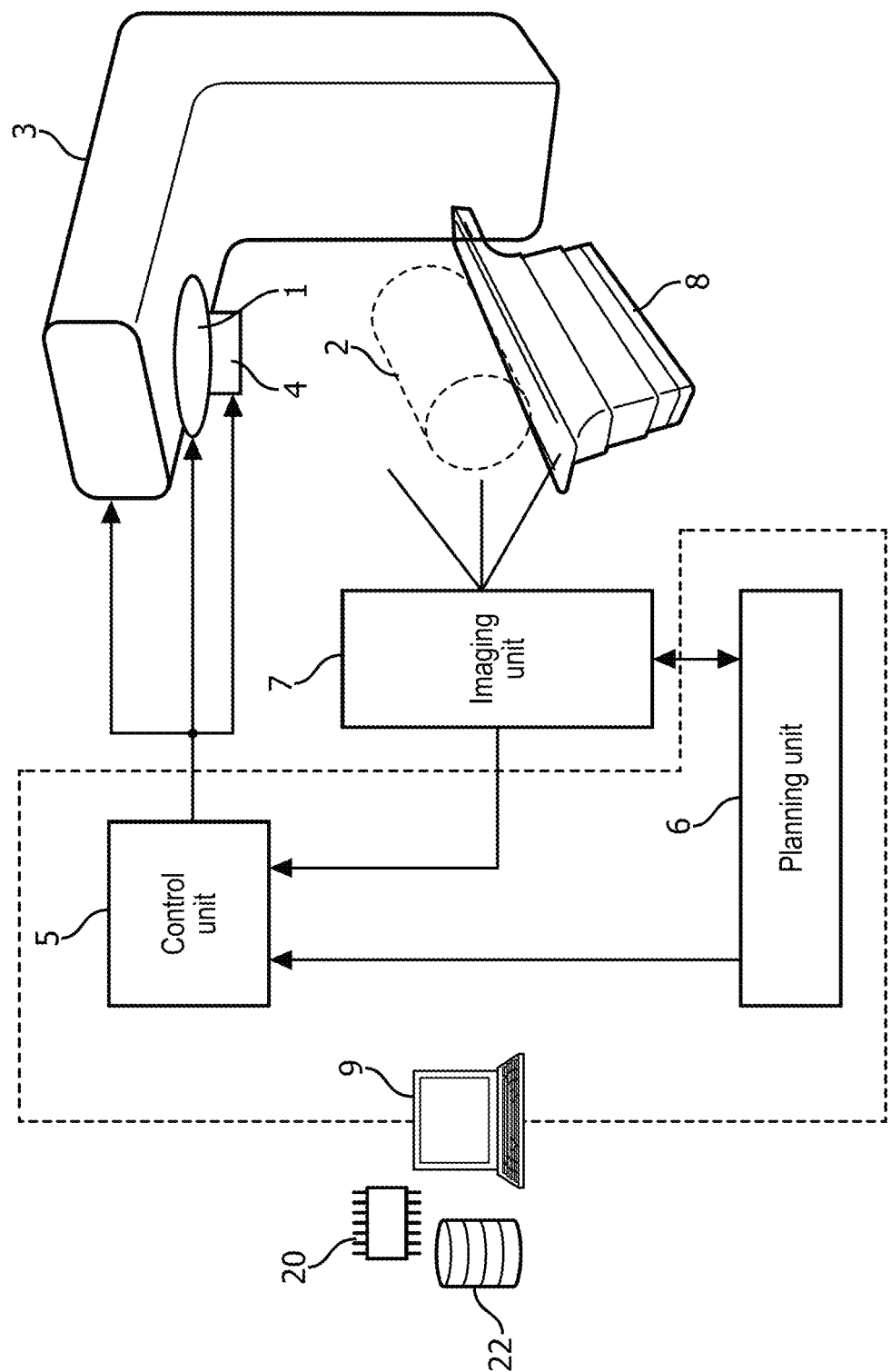
FIG. 1 schematically and exemplarily shows components of a treatment system for delivering radiation therapy treatment.

FIG. 1 schematically and exemplarily illustrates an embodiment of a treatment system for delivering a radiation therapy treatment of a target structure included in a region of a patient body. The target structure may particularly be a tumor. The treatment is delivered in accordance with a treatment plan which is generated on the basis of one or more initial treatment plans prepared a longer time, such as several days, in advance of the delivery of the treatment on the basis of a planning image. Starting from the initial treatment plan(s), an adapted treatment plan is determined shortly before the delivery of the treatment on the basis of a current image of the relevant region of the patient body. In one embodiment, this image is acquired in the treatment room. Therefore, the image is referred to as in-room image herein. However, it will be understood that the image is not necessarily acquired in the treatment in other embodiments.

In the embodiment illustrated in FIG. 1, the radiation therapy system comprises a radiation source 1, which can be operated to emit ionizing radiation into a treatment zone 2. In the treatment zone 2, the patient body is positioned on a suitable support, such as a patient table 8. The relative position and orientation of the radiation source 1 with respect to the relevant body region can be varied over a certain range of positions and orientations. For this purpose, the radiation source 1 may be mounted on rotatable gantry 3 so that the radiation source 1 can be rotated around the treatment zone 2 within a certain angular range, which may be 360° or less, in order to deliver radiation under different directions of the radiation beam. In addition, the gantry 3 and/or the patient support 9 may be movable in a direction parallel and/or perpendicular to the rotation axis of the gantry 3. Hereby, it is possible to set-up a certain relative position between the patient and radiation isocenter such that the target structure is arranged within the radiation isocenter. Further, it may be possible to rotate the patient support 8 around an axis perpendicular to the rotation axis of the gantry 3.

The radiation source 1 may include a linear particle accelerator (also known as a linear accelerator or LINAC), a cyclotron, a synchrotron or another radiation source for producing an ionizing radiation beam. Thus, both electron and proton radiation sources are contemplated. One example of another radiation source is a radioactive source, such as a cobalt source. Further, the radiation source 1 may be provided with a collimator 4 for shaping the radiation beam.

The collimator 4 may particularly allow for varying the radiation intensity across the radiation beam in a defined way. For this purpose, the collimator 4 may be configured as a multi-leaf collimator (MLC).

During delivery of the radiation therapy treatment, radiation is delivered to the target structure under varying beam directions and the intensity of the radiation emitted by the radiation source 1 may be varied in accordance with the treatment plan. Moreover, the configuration of the collimator 4 may be changed based on the treatment plan so that the radiation beam is delivered with a time-varying shape. In one implementation, the radiation therapy treatment is delivered in accordance with successive segments, where each segment corresponds to one configuration of the treatment parameters including the beam direction, the emitted radiation intensity and the collimator configuration or beam shape. In between two segments, the configuration is changed from the configuration of the first of the segments to the configuration of the second of the segments. During this period, the radiation beam may be turned off (this is usually also referred to as step-and-shoot approach). Likewise, it is possible to continuously change the configuration in accordance with the segments without interrupting the radiation beam. This approach is applied in so-called volume modulated arc therapy (VMAT), for example.

For controlling the components of the radiation therapy treatment system, including the radiation source 1, the collimator 4, the gantry 3 and the patient support 8, during the treatment, the treatment system includes a control unit 5. Preferably, the control unit 5 is implemented as a software program which comprises the control routines carried out by the control unit and which is executed in a computer device 9 coupled to the further components of the radiation therapy treatment system. The control of these components is performed in accordance with a treatment plan which specifies the corresponding control parameters, such as the parameters defining the radiation beam intensity, the collimator configuration, and the gantry position, as a function of time. These parameters are also referred to as machine parameters herein.

As said above, the treatment plan for controlling the system during the treatment is generated by adapting at least one initial treatment plan. For performing the uniadaptation the system comprises a planning unit 6. The planning unit 6 may be implemented as a software program comprising routines for performing the adaptation and for performing the adaptation of the treatment plan and being executed on a computer device 9 included in the treatment system. In this respect, the same computer device 9 may also implement the control unit 5 as explained above and as illustrated in FIG. 1. However, the planning unit 6 and the control unit 5 may likewise be implemented in different computer devices.

It should be noted that the computer or computers 9 can be variously distributed. For example, an electronic processor or processors 20 of the computer(s) 9 may include a local processor of a workstation terminal and the processor of a server computer that is accessed by the workstation terminal. (Note, the electronic processor(s) 20 is diagrammatically indicated in FIG. 1). The computer(s) 9 may also comprise a cloud computing resource. The computer(s) may include one or more displays integral with or operatively connected with the computer(s) 9. The various processing components, e.g. control unit 5 and planning unit 6, are suitably implemented by the computer(s) 9 reading and executing machine-readable instructions (e.g. software) stored on a non-transitory storage medium 22 (diagrammatically indicated in FIG. 1). The non-transitory storage medium may, by way of non-limiting illustrative example, include one or more of: a magnetic disk, RAID, or other magnetic storage medium; a solid state drive, flash drive, electronically erasable read-only memory (EEROM) or other electronic memory; an optical disk or other optical storage medium; various combinations thereof; or so forth.

The adaptation of the treatment plan is carried out on the basis of the in-room image, which is acquired shortly before the delivery of the radiation treatment. For acquiring the in-room image, the treatment system may comprise an imaging unit 7 configured in accordance with a suitable imaging modality, such as, for example, computed tomography (CT) imaging, cone-beam CT imaging or magnetic resonance imaging (MRI). That is, the imaging unit 7 may comprise a CT scanner, cone-beam CT scanner, MRI scanner, or so forth. Preferably, the imaging modality of the imaging unit 7 corresponds to the imaging modality used for acquiring the planning image. This allows for an easier and more reliable registration between the planning image and the in-room image.

In one embodiment, a single initial treatment plan is generated for a patient. This is done on the basis of a clinical prescription for the patient, which may particularly specify a radiation dose to be delivered to the target structure during the treatment. In addition, maximum radiation doses to be delivered to the organs at risk (OARs) may be specified. This may be done in the prescription for the patient and/or in general rules relating to the treatment.

Further, the initial treatment plan is prepared on the basis of a three-dimensional planning image $I_1$ of the relevant region of the patient body including the target structure which consists of voxels of a certain size. In this image, the target structure and the relevant OARs are delineated using techniques known the person skilled in the art. The delineations of the target structure and the OARs may be provided in the form of binary masks $s_i$ referring to the same coordinate frame as the planning image $I_1$. Moreover, safety margins may be added to the delineations in order to generate effective delineations of the target structure and the OARs on the basis of which the treatment plan is calculated. These safety margins account for changes of the position and/or shape of the target structure and/or the OARs during the treatment.

On the basis of the treatment goals, a set of objectives and/or constraints is determined with respect to the radiation dose to be delivered to the delineated structures. While the objectives should be fulfilled as much as possible, the constraints correspond to conditions which necessarily have to be fulfilled. Such constraints may be derived from the treatment goals. Moreover, the constraints may be feasibility constraints resulting from mechanical limitations of the treatment system.

The possible objectives and constraints relating to the target structure and the OARs particularly comprise the delivery of a maximum and minimum radiation dose to relevant structure. Minimum dose requirements usually relate to the target structure. So a minimum radiation dose to be delivered to one or more locations or regions of the target structure may particularly be specified. Maximum dose requirements usually relate to the organs at risk. In this regard, a maximum radiation dose to be delivered to one or more locations or regions of the organs at risk may particularly be specified. In addition, further objectives may be defined, such as, for example, the delivery of a uniform dose distribution to a certain region of the treatment volume (which will usually be a region of the target structure).

In the planning procedure, a treatment plan is then generated which at least approximately fulfills the objectives and which fulfills the constraints. For this purpose, an optimization problem is formulated on the basis of the objectives and constraints, and this optimization problem is at least approximately solved with respect to the relevant optimization parameters p.

For solving the optimization problem a user-guided iterative optimization procedure may particularly be applied. In each step of such a procedure, the planning system automatically calculates preliminarily optimized parameters p by approximating a solution of the optimization problem. Then, the planning system determines the dose distribution corresponding to these parameters p and visualizes the dose distribution to the planner operating the planning system. The planner reviews the dose distribution to decide whether he/she is satisfied with the dose distribution or not. If the planner is satisfied in one step, the final treatment plan is determined on the basis of the current optimized parameters p. If the user is not satisfied, the optimization problem is modified in accordance with changes specified by the user as a result of his/her review. Then, the planning system calculates a new preliminarily optimized parameters p in the next step.

In one embodiment, the optimization parameters p corresponds to the (time-varying) fluences specifying fluences of the emitted radiation beam incident onto the patient body with respect to a grid dividing the beam's cross section into elements (also referred to as beamlets), where the fluence of one element corresponds to its radiation energy integrated over time. This approach for determining the treatment plan is also referred to as fluence map optimization (FMO). From the optimized fluence map, the planning system may determine the machine parameters for achieving the fluence map using a model of the radiation source 1 and the collimator 4. These machine parameters form the treatment plan.

The dose distribution d corresponding to the fluence map, which specifies the radiation dose absorbed by each voxel of the relevant region of the patient body, can be determined using a model describing the interaction between the radiation and the tissue included in the relevant region of the patient body. More specifically, the dose distribution can be determined on the basis of an influence matrix, where each element of the each element of the influence matrix quantifies the amount of dose absorbed by a voxel of the relevant region of the patient body per unit emission intensity from one of the beamlets. The influence matrix is a function of the planning image $I_1$, particularly of the anatomical configuration of the relevant region of the patient body as shown in the planning image I, and can be determined using a technique known to the person skilled in the art.

In a further embodiment, the optimization parameters p corresponds to the machine parameters of the treatment system. This approach is also referred to as direct machine parameter optimization (DMPO). In this embodiment, a model of the radiation source 1 and the collimator, which links the fluence map with the machine parameters, is incorporated into the optimization problem so that the machine parameters are directly optimized. Using this model, the dose distribution d is included into the objective functionals $f_k$ as a function of the machine parameters in DMPO rather than as a function of the fluences.

In solving the optimization problem, an objective functional F which is generated on the basis of the objectives may particularly be minimized. The objective functional F may comprise a collection of individual objective functionals $f_k$, where each individual objective functional $f_k$ represents one objective. The objective functionals $f_k$ are generally functionals of the dose distribution d and the delineation(s) $s_i$ of the target or risk structure(s) i to which the objective relates. The dose distribution d is a function of the optimization parameters p and the anatomical configuration of the relevant region of the patient body as shown in the planning image I. Thus, providing the aforementioned dependencies in explicit form, the objective functionals $f_k$ can be written as $f_k(d[p,I], s_i)$.

The objective functional F may particularly correspond to a weighted sum of the objective functionals $f_k$, i.e.

$$F(p) = \sum_{k=1}^{N} w_k \cdot f_k(d[p, I], s_i) \quad (1)$$

where the parameter $w_k$ denotes the weight of the objective function $f_k$. Due to the weighting, objectives having a higher weight are satisfied more likely than objectives having a lower weight, in case such objectives are in conflict with each other. Hence, the weights are selected in accordance with the importance of the objectives with respect to the success of the treatment.

Further, as a specific example, an objective functional $f_k$ representing an objective to deliver a maximum or minimum radiation dose D to a certain volume V pertaining to a target or risk structure may be given in the form of a quadratic cost function by $$f_k = \sum_{i \in V} g(d_i[p, I], D) \cdot \left[\frac{d_i[p, I] - D}{D}\right]^2 \cdot \Delta v_i \quad (2)$$

where $g=H(d_i-D)$ in case a maximum dose D is specified and $g=H(D-d_i)$ in case a minimum dose D is specified, $\Delta v_i$ denotes the volume of the voxel i, H is the Heaviside step function defined by $$H(x) = \begin{cases} 0, & x < 0 \\ 1, & x \geq 0 \end{cases} \quad (3)$$

In each step of the user-guided optimization procedure one version of the objective functional F may be minimized with respect to the optimization parameters p such that the constraints are fulfilled. For this purpose, the planning system can apply any suitable numerical algorithm known to the person skilled in the art. Then, the dose distribution corresponding to the optimized parameters p is presented to the planner as explained above. When the planner is not satisfied with this dose distribution, he/she may modify the objective function F to create a new version thereof which is then minimized again in the next step of the procedure. In the process of modifying the objective function F, the planner may particularly adapt one or more weights $w_k$ and/or change the individual objective functionals $f_k$, e.g. by deleting and/or adding objective functionals $f_k$. Once, the planner is satisfied with the dose distribution, the initial treatment plan is generated on the basis of the optimized parameter $p_1$ corresponding to the accepted dose distribution $d_1$ as explained above.

In the way described above, the initial treatment plan is prepared some time in advance of the delivery of the radiation therapy treatment in a planning system which may be included in the treatment system or which may be operated separately. Since the anatomical configuration of the region of the patent body including the target structure may change between the time of generation of the initial treatment plan and the time of the delivery of the radiation treatment, an adaptation of the treatment plan is carried out on the basis of the in-room image $I_2$ by means of the planning unit.

In order to prepare the adaptation, the delineations $s_i'$ of the target structure and the relevant OARs in the in-room image are determined. This may be done by newly delineating these structures in the in-room image. However, it is preferred that the delineations $s_i'$ are determined on the basis of the planning image $I_1$ using an image registration procedure. In particular, deformable image registration (DIR) may be carried out between the planning image $I_1$ and the in-room image $I_2$ in order to determine a transformation for mapping the planning image $I_1$ onto the in-room image $I_2$. Using this transformation, the delineations $s_i'$ of the relevant structures in the in-room image $I_2$ may be determined from the delineations $s_i$ of the structures in the planning image $I_1$.

The adaptation of the treatment plan is carried out in the planning unit 6 on the basis of a rigid transformation T determined by the planning unit 6. This is a transformation which only comprises a common rotation and/or a translation of voxels in the image space.

In accordance with a first approach, the transformation is used in order to transform the beam configuration as specified in the initial treatment plan in order to determine the corresponding treatment parameters of the adapted treatment. In this process, the beam directions may particularly be changed (e.g. by specifying a rotation of the grantry 3) and/or the beam may be rotated around the beam axis (e.g. by specifying a rotation of the collimator 4) on the basis of a part of the transformation which corresponds to a rotation, and the relative positions between the radiation isocenter and the patient may be changed (e.g. by specifying a displacement of the gantry 3 and or the patient support) on the basis of a part of the transformation which corresponds to a translation. By means of the latter change, it is particularly possible to compensate for displacements of the target structure within the patient anatomy from its position at the time of the initial planning.

In accordance with a further approach, the transformation T or its inverse may be used for transforming the dose distribution d corresponding to the initial treatment plan to an adapted dose distribution $d_2$. On the basis of this dose distribution the adapted treatment plan may then be determined. This may be done by determining a fluence map resulting in the adapted dose distribution $d_2$. This determination can be made on the basis of the (inverse) influence matrix for the anatomical configuration of the relevant body region as shown in the in-room image $I_2$. Further, the planning unit 6 may determine the machine parameters for the adapted treatment plan on the basis of the fluence map using a model of the radiation source 1 and the collimator 4.

For determining the rigid transformation T, the planning unit 6 uses a functional F', which is determined on the basis of the treatment objectives and which is (approximately) minimized by the optimization parameters $p_1$ corresponding to the initial treatment plan. The functional F' is created on the basis of the transform T. More specifically, the functional F' is created on the basis of a transform $T^*I_2$ of the in-room image $I_2$ and on the basis of a transform $T^*s_{2i}$ of the delineations of the target structure and the OARs in the in-room image $I_2$ and is evaluated for the optimization parameters $p_1$. Thus, the functional F' has the form $$F'(T)=F'(d[p_1,T^*I_2],T^*s_{2i}) \quad (4)$$

The transform $T^*I_2$ of the in-room image $I_2$ and the transform $T^*s_{2i}$ of the delineations of the target structure and the OARs in the in-room image $I_2$ have the form $$T^*I_2(x)=I_2(Rx+t) \quad (5)$$

and $$T^*s_{2i}(x)=s_{2i}(Rx+t) \quad (6)$$

where R is a rotation matrix, t represents a displacement and x denotes the voxel positions in the image space. With respect to the dependency of the functional F'(T) on the transform $T^*I_2$ of the in-room image $I_2$, the functional F'(T) may particularly depend on an influence matrix determined in accordance with the anatomical configuration of the relevant body region as represented by the transformed image $T^*I_2$. This dependency corresponds to the dependency of the objective functional F on the planning image $I_1$, which already has been explained above.

In a specific implementation, the planning unit 6 may create the functional F(T) on the basis of the objective functional F which was used in the planning procedure for determining the initial treatment plan and which is minimized by the optimization parameters $p_1$ corresponding to the initial treatment plan. In particular, the functional F'(T) may correspond to the version of the objective function F used in the last step of the operator-guided iterative planning procedure, which resulted in the accepted dose distribution $d_1$. However, the parameters of the objective function which were determined on the basis of the planning image I and on the basis of the delineations $s_{1i}$ of the target structure and the relevant OARs in the planning image $I_1$ in the planning procedure are replaced by corresponding parameters determined on the basis of the transformed in-room image $T^*I_2$ and the transformed delineations $s_{2i}$. Thus, the functional F'(T) may have the form $$F'(T) = \sum_{k=1}^{N} w_k \cdot f_k(d[p_1, T * I_2], T * s_{2i}) \quad (7)$$

and the weights $w_k$ and the functionals $f_k$ may corresponds to those used in the initial planning procedure.

Upon having generated the functional F'(T), the planning unit 6 minimizes the minimizes the functional F'(T) with respect to the transformation T. Upon having determined a specific transformation T by at least approximately minimizing the functional F(T), the planning unit 6 determines an adapted treatment plan in a way explained above. Thus, the planning unit 6 directly determines adapted treatment parameters, particularly adapted beam directions and adapted positions of the radiation isocenter relative to the patient, using the transformation. Or, the planning unit 6 may determine the inverse of the determined transformation T and may use the inverse in order to generate an adapted dose distribution on the basis of which the treatment plan is generated as explained above.

One may think of the determined transformation T as an approximation of a transformation for transforming the in-room image $I_2$ into the planning image $I_1$. However, the transformation is not determined on the basis of a comparison of characteristics of the images or anatomical configurations shown therein but on the basis of the dose objectives.

In a variant of the embodiments described so far, plural initial treatment plans may be generated in the initial planning procedure. The different initial treatment plans may be generated on the basis of different safety margins for the target structure and the OARs or on the basis of different settings of the radiation source which result in dose distributions all satisfying the planning objectives. In addition or as an alternative, the initial treatment plans may be generated for different anatomical configurations of the relevant region of the patient body. These anatomical configurations may include anticipated likely changes to the anatomical configuration represented by the planning image. Such changes may be determined on the basis of empirical observations for the same region of the patient body for a number of other patients and/or on the basis of models describing the progression of the target structure with time, for example).

When plural initial treatment plans are prepared, one transformation S (or T) may be determined by the planning unit 6 for each of the treatment plans on the basis of the in-room image as described above. Then, the planning unit 6 may compare the determined minima of the functional F'(T) for the different treatment plans. Upon the comparison, the planning unit 6 may select the treatment plan having the smallest minimum and adapts this treatment plan on the basis of the transformation S determined for this treatment plan. The adapted treatment plan may then be used to deliver the radiation therapy treatment to the patient.

In a further implementation, the planning unit 6 may adapt several initial treatment plans on the basis of the transformations S determined for these treatment plans and combines the adapted treatment plans to generate a treatment plan which is then used to deliver the radiation therapy treatment. The combination may particularly be a weighted combination, where the weights may be determined on the basis of the minima of the functionals F'(T) evaluated for the different treatment plans. In the process of combing the treatment plans, the planning unit may determine a treatment plan, which comprises segments from the each of the combined treatment plans so that the segments are delivered one after the other.

In embodiments disclosed herein, only a forward calculation of the dose d is computed, which improves computational efficiency. Nonetheless, optimization of the objective functional F(d,T) with respect to the rigid transformation T is still computationally intensive. In particular, each iteration of the optimization entails computing the derivatives of the functional F(T) with respect to dose distribution d and the rigid transformation T. The derivatives with respect to the dose distribution, in particular, are computationally expensive. For example, to calculate the three-dimensional (spatial) derivative involves computing at least four distinct dose distributions: $d(x,y,z)$, $d(x+\Delta, y, z)$, $d(x, y+\Delta, z)$, and $d(x, y, z+\Delta)$. Each of these requires calling the dose engine to perform the computationally expensive dose distribution computation.

It is recognized herein that the partial derivative of the objective functional F(d,T) with respect to T usually dominates over the partial derivative of F(d,T) with respect to the dose distribution d. In view of this, in some further illustrative embodiments described next, the optimization is recast as a more efficient iterative process. In each pass, a dose distribution $d_0$ is computed for a shift vector $\delta$. Then, a dosimetric patient setup optimization optimizes the objective functional $F(T|d_0)$. This is alternatively written as $f(d_o, T\delta)$ in the formalism employed in describing these embodiments, where $\delta$ is the shift vector with no rotation component (that is, the rigid transformation has the rotation matrix R set to no rotation and the shift vector $\delta$ is then the displacement vector t), and $T\delta$ is a shifted region of interest (ROI) mask) with respect only to the shift vector $\delta$. The optimization of the objective functional $f(d_o, T\delta)$ uses only the partial derivative with respect to $T\delta$ but not the partial derivative with respect to the dose $d_o$.

As shown by simulations disclosed hereinafter, only a few iterations (i.e., less than a half-dozen) was sufficient to achieve a converged value for $\delta$. However, even a single iteration provides a substantial improvement. Additionally, while the illustrative embodiments set the rotation matrix R of the rigid transformation to implement no rotation, it is straightforward to incorporate optimization of a rotation component R as well. In practice, however, some commercially available embodiments of the patient support $\delta$ do not provide a useful range of rotation adjustment, so that adapting the radiation therapy by way of both rigid shift and rigid rotation is not practical with such patient supports.

As with the previous embodiments, the output is the optimized shift vector $\delta$ (or, the optimized rigid transform T also including rotation). Thus, the beam parameters of the radiation therapy plan are not adjusted, and in some jurisdictions there may be no need to reassess quality assurance (QA) metrics.

Figure 2:
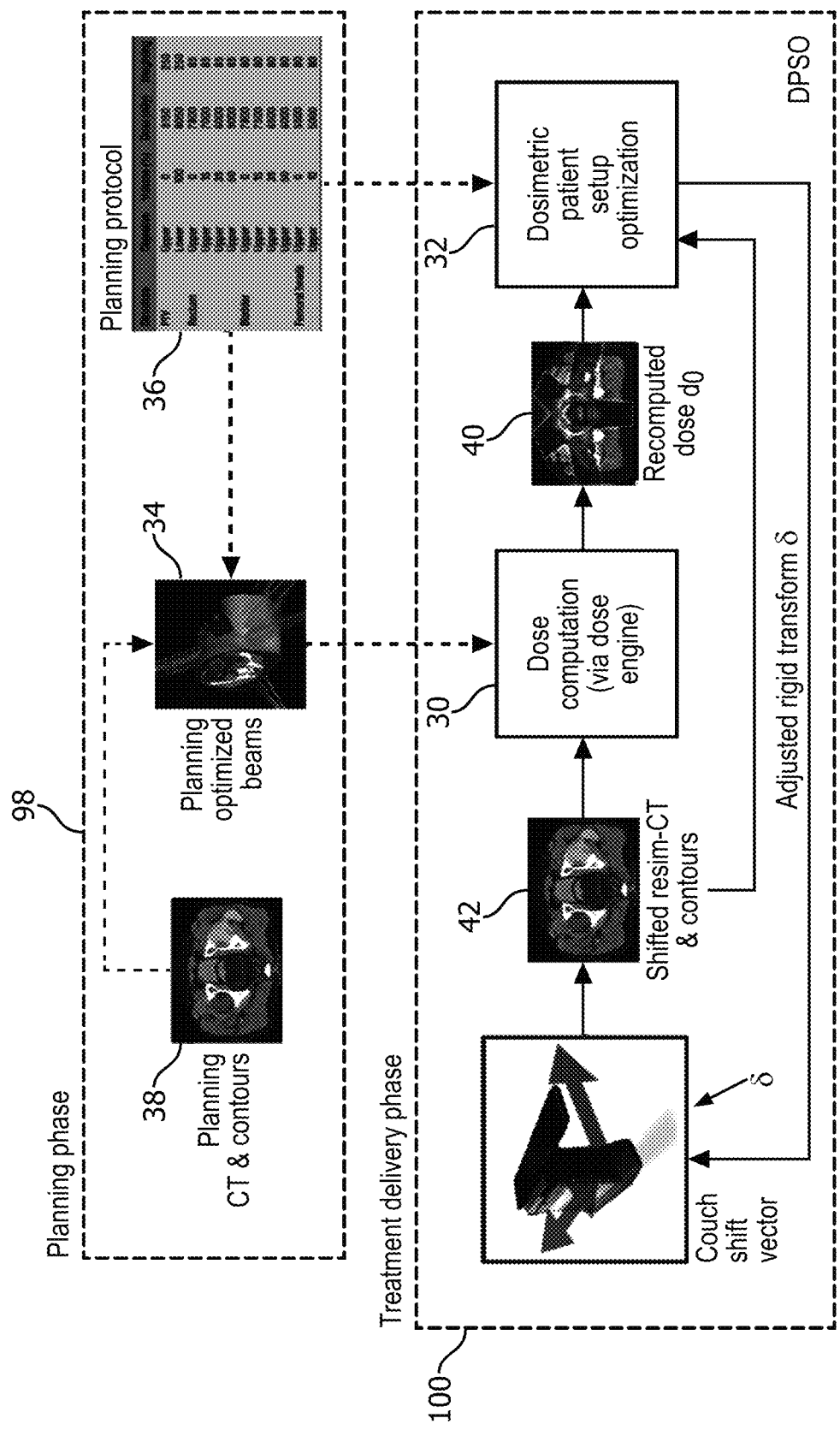
FIG. 2 diagrammatically shows a treatment planning system according to another aspect.

With reference now to FIG. 2, the planning unit 6 in some embodiments is configured to perform an iterative adaptive treatment planning method or process 100, also referred to herein as a dosimetric patient setup optimization (DPSO) 100, which as diagrammatically shown in FIG. 2 includes implementing: a dose computation module 30; and a dosimetric patient setup optimization module 32. The DPSO 100 operates to adapt a treatment plan produced by a radiation therapy planning process 98, which may for example employ inverse planning of intensity modulated radiation therapy (IMRT), volume modulated arc therapy (VMAT), or another radiation treatment protocol. As input, the dose computation module 30 receives a set of treatment planning optimized beams 34 generated from a planning protocol 36 of the planning process 98, and planning CT and contours 38 from a CT image of the patient which were used by the planning process 98. The dose computation module 30 calculates a recomputed dose 40 from the optimized beams 34. The recomputed dose 40 (also denoted $d_0$ herein) and the planning protocol 36 are then input into the dosimetric patient setup optimization module 32. The dosimetric patient setup optimization module 32 calculates a couch shift vector $\delta$ of the patient support 8. The term 'optimization' and similar phraseology as used herein is to be understood as broadly encompassing optimizations that terminate prior to reaching the globally optimal value of the objective function (for example, terminating when an iteration-over-iteration improvement is less than some stopping criterion, or terminating after a fixed number of iterations of the optimization), optimizations that terminate at a local minimum (or maximum, depending on the optimization formalism), or so forth. The transformation comprises the rigid spatial transform (T) updated by the last adjustment iteration.

In an iterative process, the determined couch shift vector $\delta$ can be used to generate a shifted re-simulated CT image and contours 42, which serves to supplement the planning CT and contours 38. The updated contours 42 are input to the dose computation module 30 and used to generate another recomputed dose 40. The iterative process repeats until the determined couch shift vector δ stabilizes (e.g., does not fluctuate).

Figure 3:
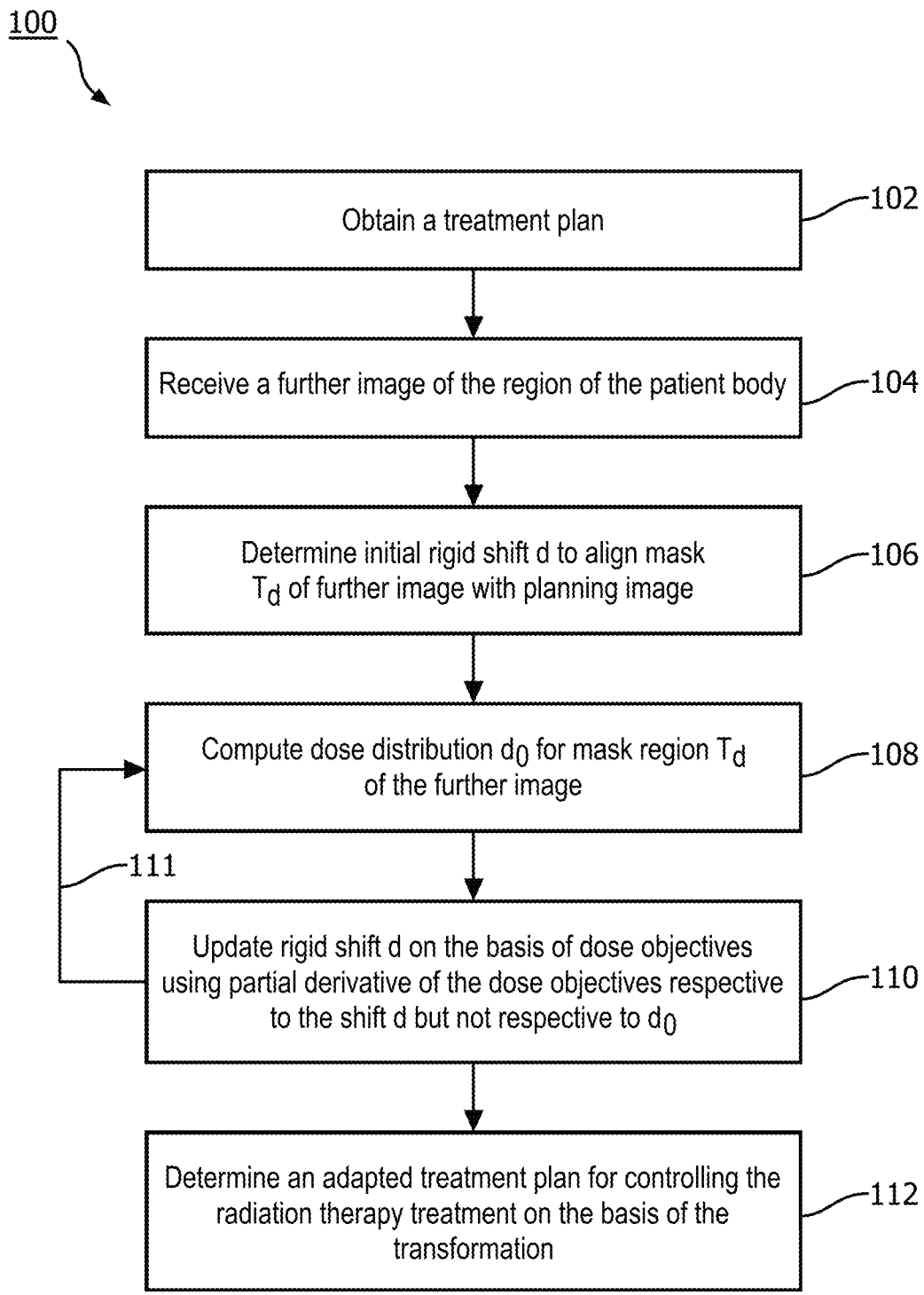
FIG. 3 shows exemplary flow chart operations of the system of FIG. 1.

With reference to FIG. 3, an illustrative embodiment of the treatment planning method 100 is diagrammatically shown as a flowchart. At 102, the at least one electronic processor 20 is programmed to obtain a treatment plan. The treatment plan was previously generated by the planning process 98 on the basis of a planning image of a region of a patient body and on the basis of dose objectives ($f$) with respect to the region of the patient body. The treatment plan corresponds to a dose distribution in the region of the patient body. In some examples, the treatment plan can be retrieved from the one or more databases or non-transitory storage media.

At 104, the at least one electronic processor 20 is programmed to receive a further image of the region of the patient body. In some examples, the at least one electronic processor 20 is programmed to control the imaging device 16 to acquire the further image of the region of the patient body. Typically, the further image is taken with the patient positioned on the patient support 8 with restraints in place positioning the patient for receiving the radiation therapy. In some embodiments, the imaging device 16 is mounted on the gantry 3 or otherwise secured with and integral to the radiation therapy delivery device so as to acquire the further image as an in-treatment room image—in this way the potential for movement of the patient between acquisition of the further image and final preparations for delivery of the therapeutic radiation is minimized. The tumor and organs at risk (OARs) are outlined in the further image to define a region of interest (ROI) mask. This can be done manually, or by a non-rigid (e.g. deformable) partial registration of the further image and the planning image (for which tumor and OAR outlines were generated during the planning process 98) and mapping of the planning image outlines to the spatially registered further image, or by some combination of automated and manual processing (e.g., nonrigid spatial registration and outline mapping followed by optional manual adjustment of the outlines in the further image).

At 106, an initial value for the rigid shift δ is determined to align the shifted region of interest (ROI) mask $\tau_\delta$ with the corresponding ROI mask of the planning image. This can be done by performing a rigid spatial registration of the ROI mask of the further image and the corresponding ROI mask of the planning image.

The iterative loop of the DPSO 100 begins at 108. At 108 the dose computation module 30 (see FIG. 2) computes the dose distribution $d_0$ for the ROI mask $\tau_\delta$ of the further image. This can be done, for example, by calling an existing dose engine such as one used in the planning process 98, with the beam parameters of the (already optimized) radiation treatment plan generated by the planning process 98.

At 110, the dosimetric patient setup optimization 32 (see FIG. 2) updates the rigid shift δ on the basis of the dose objectives ($f$) using a partial derivative of the dose objectives with respect to the rigid spatial transform (δ) but not using a partial derivative of the dose objectives with respect to the dose distribution ($d_0$). In principle, this optimization should employ the full derivative of the dose objectives respective to both the dose distribution $d_0$ and the transformation δ (or, equivalently, $\tau_\delta$). However, it is recognized herein that the derivative with respect to the transformation δ should dominate over the derivative with respect to the dose distribution $d_0$ such that the latter can be neglected in computing the derivatives for use in the optimization.

The output of the step 110 is an adjusted rigid transform δ. Advantageously, this update process 108, 110 requires only a single dose distribution computation 108. This computationally efficient processing is achieved by neglecting the partial derivatives of the dose objectives $f$ respective to the dose distribution.

It is contemplated to terminate the DPSO process with this value; however, in the illustrative embodiments, and as indicated by a diagrammatic flow arrow 111 in FIG. 3, the operations 108, 110 may be iterated to iteratively improve the rigid transformation δ. The iterative process, if performed, can be repeated for a fixed number of iterations, or until some stopping criterion is met, such as the iteration-over-iteration change in δ being less than some threshold, or some combination of stopping criteria may be employed (e.g. stop when the iteration-over-iteration change in δ is less than some threshold or when a maximum N iterations are performed where N is some chosen integer. In simulations reported later herein, it was found that only a few iterations are needed, e.g. N<6 is suitable in some embodiments.

At 112, the at least one electronic processor 20 is programmed to determine an adapted treatment plan for controlling the radiation therapy treatment on the basis of the transformation. In one example, the treatment plan is adapted to generate an adapted treatment plan which includes an adjustment by the determined or updated rigid spatial transform (T) (corresponding to the rigid shift δ of the last iteration of the loop 108, 110) of patient position respective to the radiation treatment device 12. In one example, the determining of the adapted treatment plan includes determining an adjustment of the patient support 8 or of a position of the radiation therapy device 1, 3 respective to the patient support 8. Typically, the determining of the adapted treatment plan does not include determining adjustments to beam parameters of the treatment plan. The beam parameters can include radiation source parameters, multi-leaf collimator (MLC) settings, or other adjustments to the applied therapeutic radiation beams.

In the following, some further examples of the dosimetric patient setup optimization (DPSO) 100 are described.

Radiation therapy plans such as direct machine parameter optimization (DMPO) or volumetric modulated arc therapy (VMAT) plans are usually generated via optimization problems where a dosimetric function $f$ is minimized to find a best set of delivery parameters. A given initial treatment plan (e.g. a set of optimal beams, VMAT are control points, etc.) is estimated, and the corresponding dose distribution $d_0$ satisfying a given clinical protocol (i.e. a list of dose objectives/constraints) is generated. A typical dose objective $f$ is function of the dose distribution $d(x)$ and the segmented anatomical region of interest (ROI) binary mask $\tau(x)$, and can be given as Equation 1:

$$f = f(d,\tau) = f(d(x), \tau(x)) \tag{8}$$

The differential of the dose objectives $f$ with respect to the dose d and the structure binary mask τ is given as Equation 9:

$$\frac{df}{dx}(x_0) = \frac{df}{dx}(d(x_0), \tau(x_0)) \tag{9}$$
$$= \frac{\partial f(d, \tau_0)}{\partial d}(d_0)\frac{\partial d}{\partial x}(x_0) + \frac{\partial f(d_0, \tau)}{\partial \tau}(\tau_0)\frac{\partial \tau}{\partial x}(x_0)$$

where $x_0$ represents the grid spatial positions of the voxels in the planning image $I(x_0)$ (e.g. a planning CT image), $d_0 = d(I_0) = d(I(x_0))$ is the initial dose distribution computed using a pre-optimized radiation therapy plan and the planning image $I(x_0)$, and $\tau_0 = \tau(x_0)$ is a segmented ROI binary mask at the given planning image $I(x_0)$, respectively.

Evaluation of Equation (9) is computationally expensive in substantial part due to the need to compute the partial derivatives $$\frac{\partial f(d, \tau_0)}{\partial d}(d_0)\frac{\partial d}{\partial x}(x_0)$$

of the dose objectives $f$ respective to the dose distribution $d_0$. Computing these partial derivatives would require invoking the dose engine to compute the dose distribution for various spatial differentials, e.g. for the shift dx in the x-direction, the shift dy in the y-direction, and the shift dz in the z-direction (using conventional x, y, z Cartesian coordinate notation). However, it is recognized herein that the partial derivatives $$\frac{\partial f(d_0, \tau)}{\partial \tau}(\tau_0)\frac{\partial \tau}{\partial x}(x_0)$$

of the close objectives $f$ respective to the rigid shift $\delta$ dominate over the partial derivatives respective to the dose distribution, and hence the latter can be neglected.

Taking this approach, the partial derivative of the dose objectives $f$ with respect to the dose d are neglected, and hence the differential of $f$ given in Equation 9 can be simplified as expressed in the following Equation 10:

$$\frac{df}{dx}(x_0) \cong \frac{\partial f(d_0, \tau)}{\partial \tau}(\tau_0)\frac{\partial \tau}{\partial x}(x_0) \tag{10}$$

Standard IMRT dose objectives are given as ROI-weighted squared two- and/or one-sided penalty functions expressed as Equation 11:

$$f(d_0, \tau) = \frac{\sum_i \tau(x_i)P(d_0(x_i))}{\sum_i \tau(x_i)} \tag{11}$$

where P represents a generic dosimetric penalty function (e.g. minimum, maximum, uniform dose, maxEUD, maxDVH, etc.), and $\tau(x_i)$ are ROI mask weights in [0,1] at voxel spatial positions $x_i$.

For the sake of simplicity, only a tridimensional shift $\delta$ vector is used to register the planning image to the further image (in other words, the rotation matrix is not employed), and $\delta$-shifted ROI masks can be given by Equation 12:

$$\tau_\delta(x) = \tau(x - \delta) \tag{12}$$

As the shift $\delta$ is rigid, this yields:

$$\sum_i \tau(x_i - \delta) = \sum_i \tau(x_i) = N_\tau \tag{13}$$

The dose objective function can be rewritten as a function of the shift $\delta$ vector:

$$f(d_0, \tau, \delta) = \frac{\sum_i \tau_\delta(x_i)P(d_0(x_i))}{N_\tau} = \frac{\sum_i \tau(x_i - \delta)P(d_0(x_i))}{N_\tau} \tag{14}$$

in which, the dose $d_0$ is fixed during the dosimetric registration optimization performed to find the optimal shift $\delta$ vector.

The derivative off $f$ with respect to the shift $\delta$ vector is given by Equation 15:

$$\frac{\partial f}{\partial \delta} = \frac{\sum_i \frac{\partial \tau}{\partial \delta}(x_i - \delta)P(d_0(x_i))}{N_\tau} = -\frac{\sum_i \frac{\partial \tau}{\partial x}(x_i - \delta)P(d_0(x_i))}{N_\tau} \tag{15}$$

A B-splines interpolator (see, e.g., M. Unser, "Splines: A perfect fit for signal and image processing", IEEE Sig. Proc. Mag., vol. 16, pp. 22-38, 1999) is used to both interpolate the ROI masks $\tau(x)$ and its spatial derivatives $$\frac{\partial \tau}{\partial x}(x)$$

at shifted positions $(x_i - \delta)$ as Equation 16:

$$\tau(x) = \sum_{j \in J_c} c_j \beta_3(x - j). \tag{16}$$

in which $\beta_3$ is a 3D tensor product of 1D centered B-splines.

The optimal shift $\delta$ vector minimizing the dose objective $f$ can be computed using a gradient-based solver. At each iteration, the dosimetric patient setup optimization (DPSO) method 100 toggles between dose re-computation 30, 108 using a fixed $\delta$-shifted image and ROI masks $\tau$, and shift $\delta$ vector optimization 32, 110 at a fixed re-computed dose $d_0$ until a given stopping criteria is satisfied (e.g. maximum number of iterations, relative function tolerance, etc).

As previously noted, while in the illustrative embodiments the rigid spatial transform $\delta$ is a rigid translational shift (with no rotation), in other embodiments the rigid spatial transform $\delta$ may include both rigid translational shift and rigid rotation components (e.g. as express in Equations 5 and 6).

Figure 4:
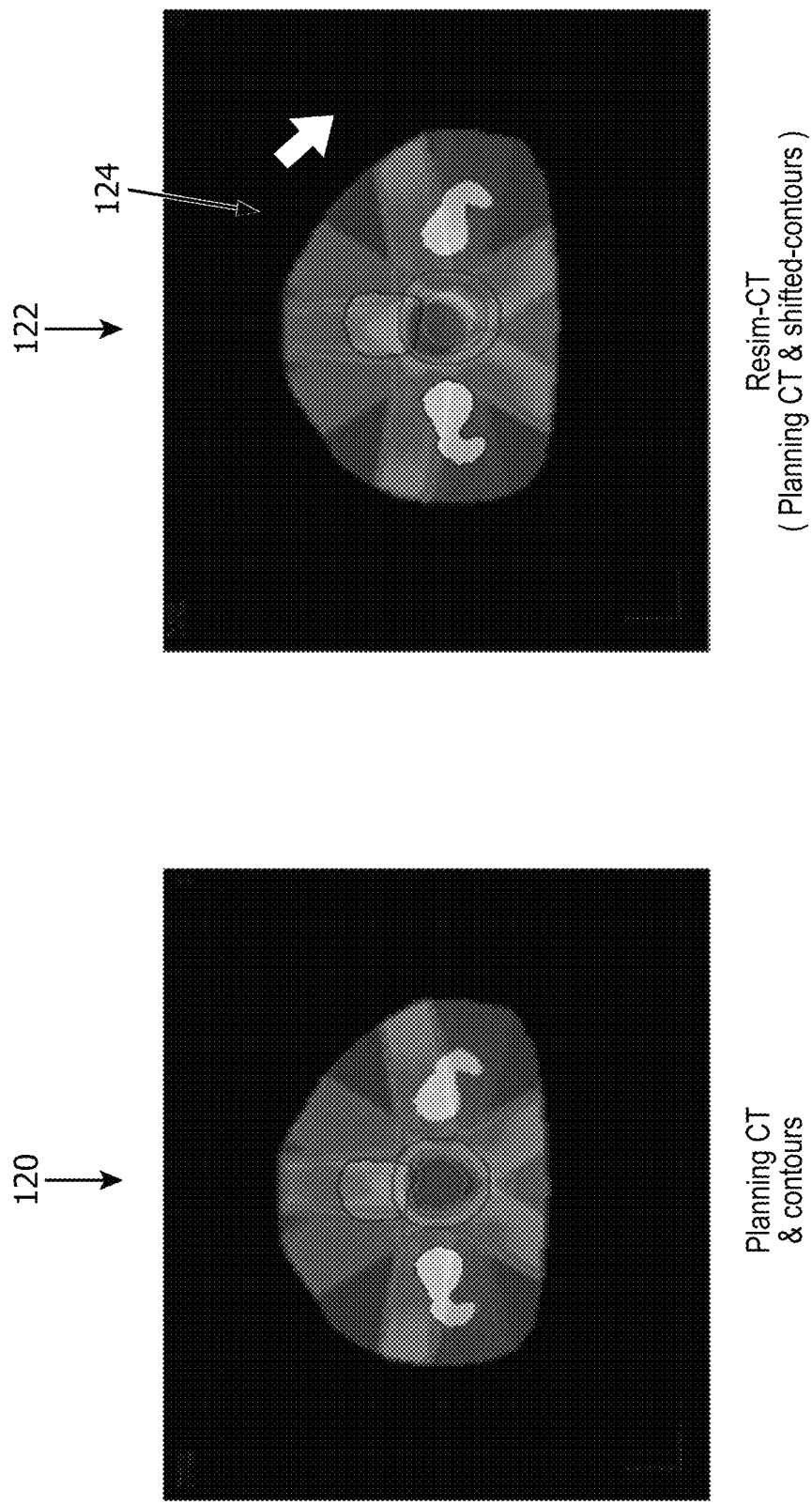

The DPSO method 100 was validated over a prostate phantom and a clinical HN dataset (named HN10). For the prostate phantom case, a shift of 1.25 cm was enforced on x-y directions only. FIG. 4 shows, on a left side 120, the phantom planning CT and the dose distribution, and a right side 122 shows a shifted re-simulated-CT image and the re-computed dose. Here the arrows 124 indicate the direction of the applied shift vector $\delta(x, y, z) = (1.25, 1.25, 0)$ cm.

Figure 5:
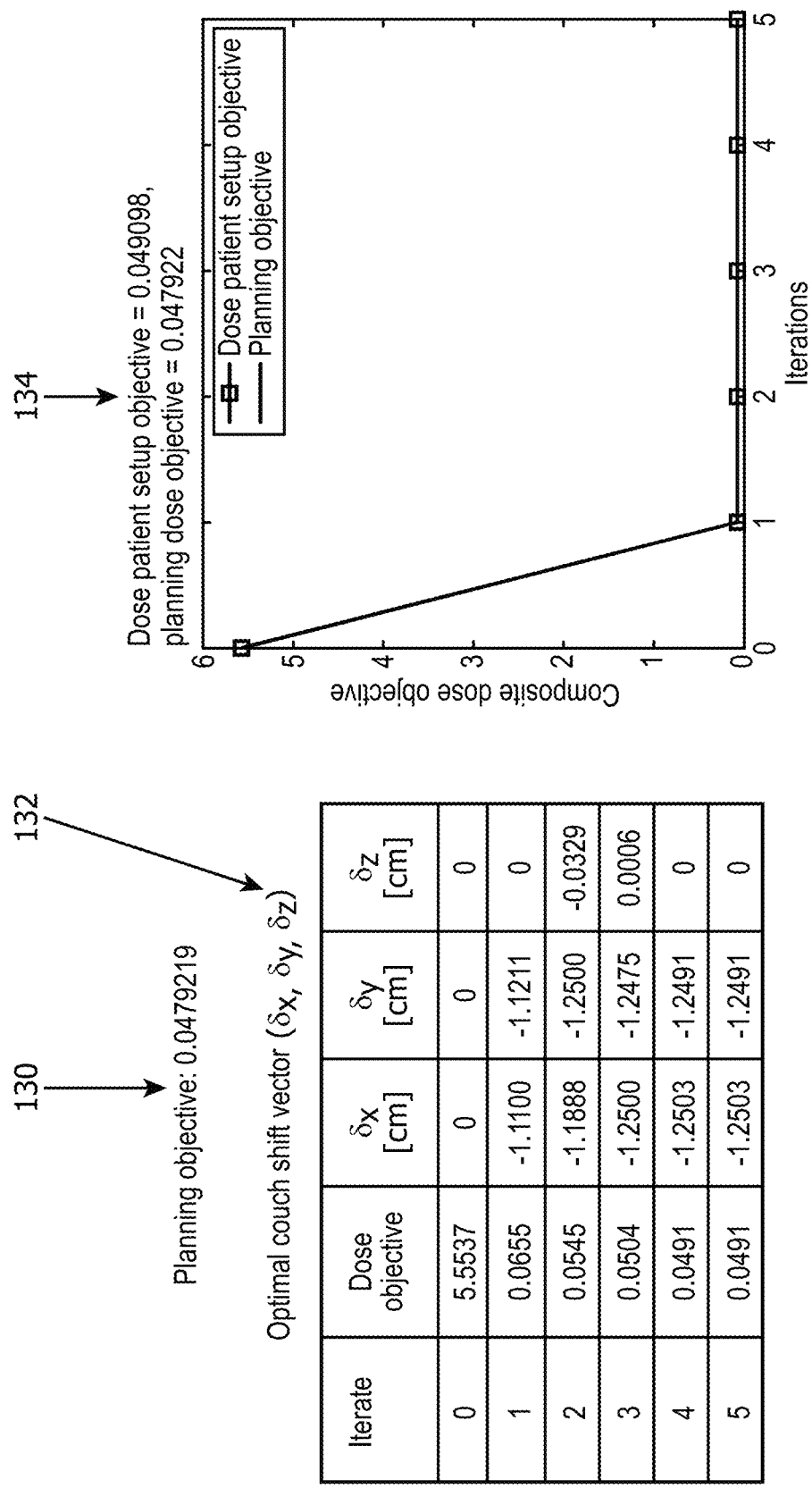

FIG. 5 shows, on a left side, an initial planning dose objective value 130 having a value of $f = 0.0479$, a table 132 with the dose objective values and corresponding optimal $\delta$ vectors at different DPSO iterations, and a right side shows a plot 134 of the dose objective values. It is seen that after 2-3 iterations the DSPO iteration converged to a minimum. The objective value factor (with respect to the planning objective value) was reduced from 115.89 to 1.02.

Figure 6:
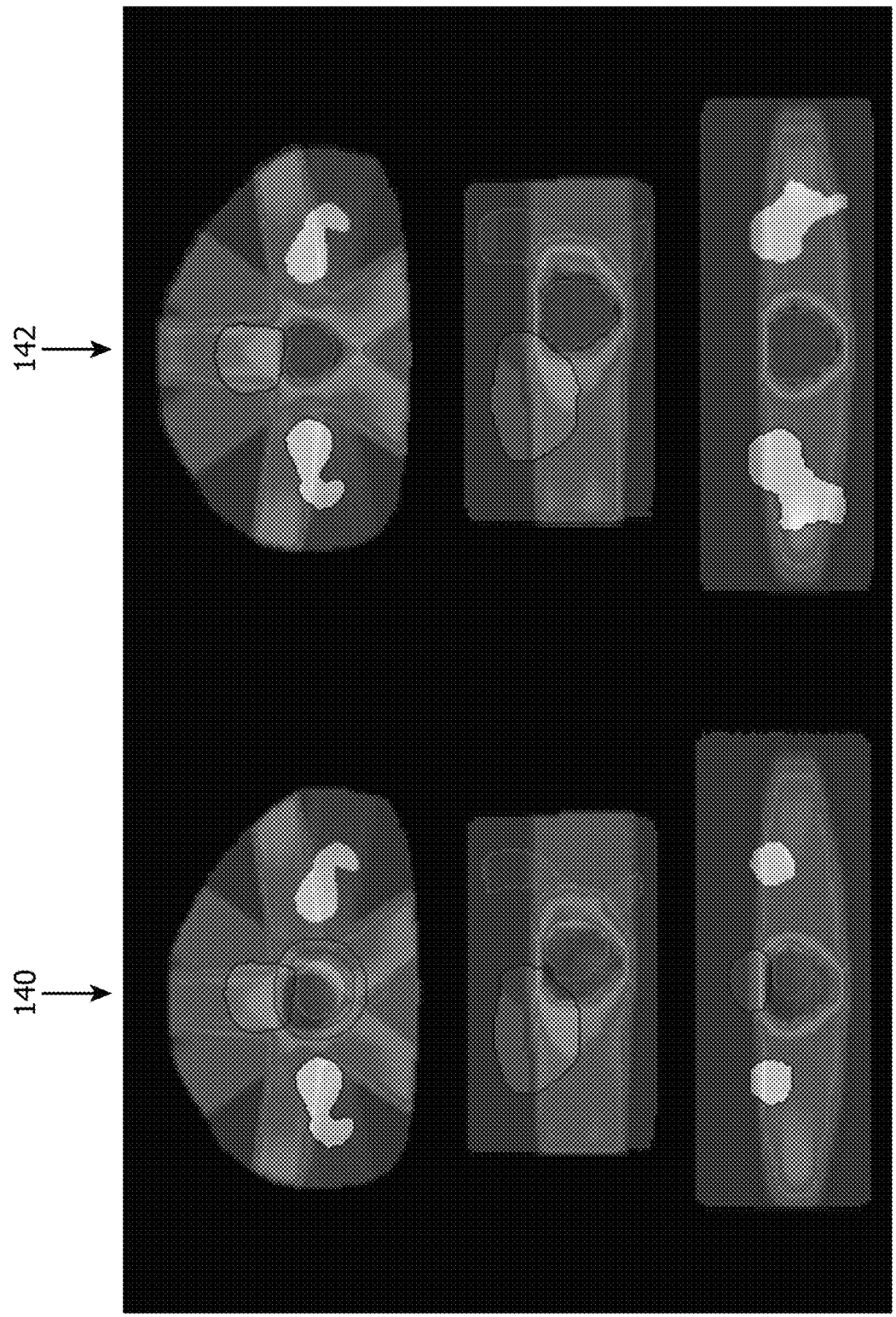

FIG. 6 shows a prostate phantom dataset. A left side 140 shows a re-simulated-CT image and re-computed dose distribution, and a right side 142 shows the optimal DPSO shifted CT image and corresponding re-computed dose distribution.

FIG. 7 shows a regional dose statistics for the prostate phantom dataset. The top row shows original planning dose statistics, the middle row shows dose statistics for the initial shifted re-simulated-CT, and the bottom row shows regional dose statistics when shifting the re-simulated-CT via DPSO.

Figure 8:
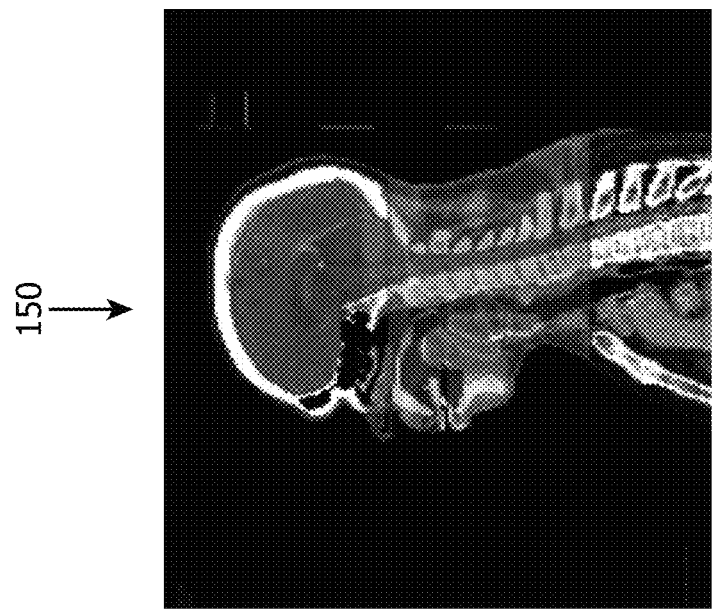
Figure 8:
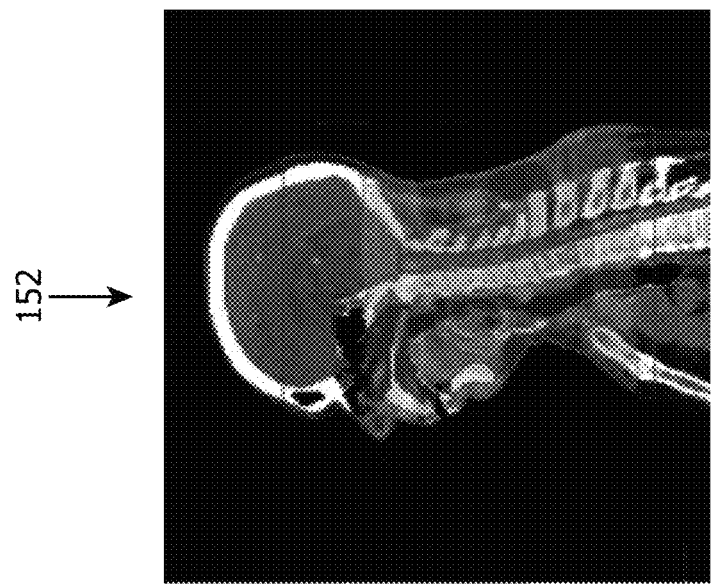
Figure 9:
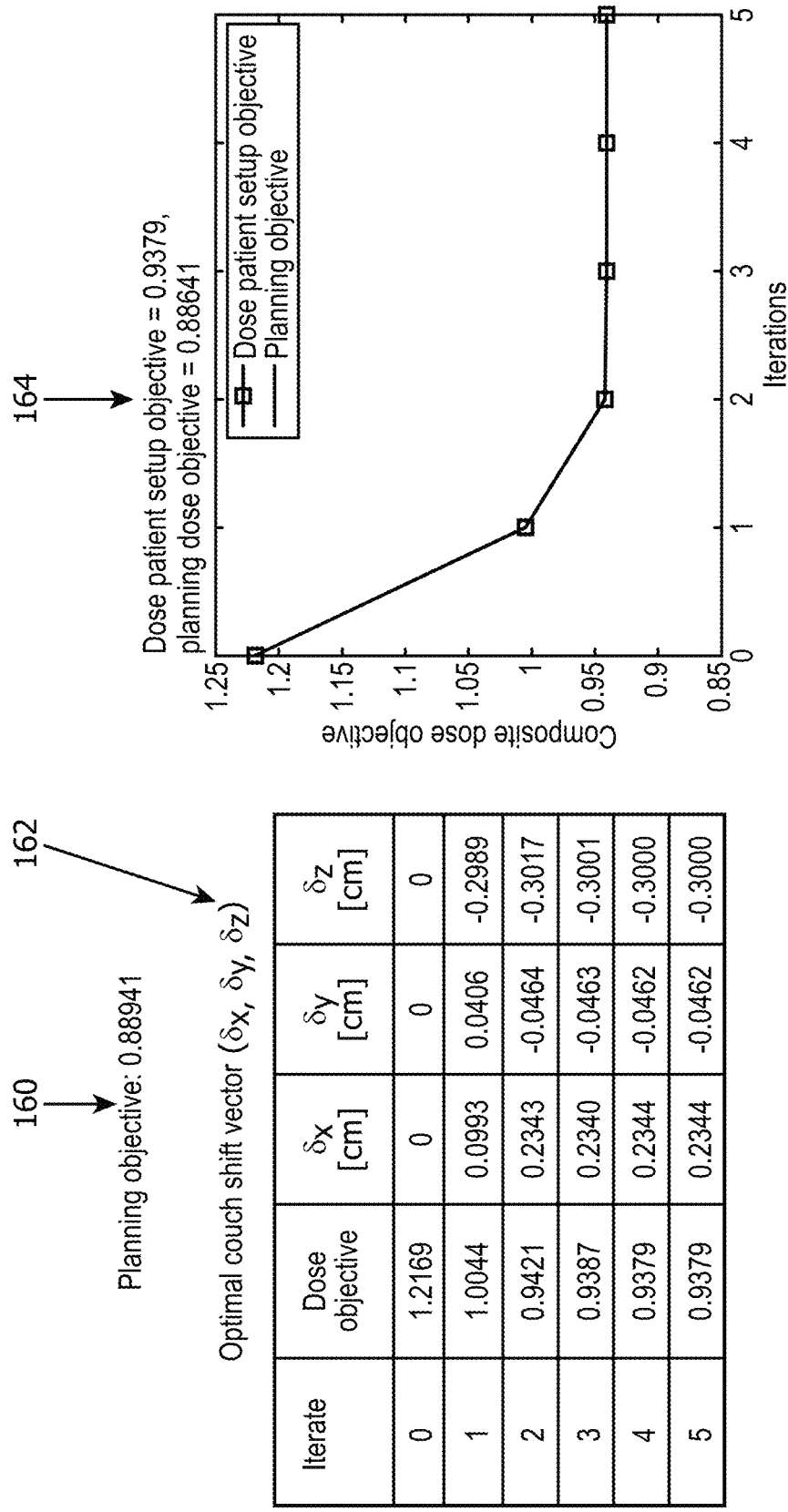
Figure 10:
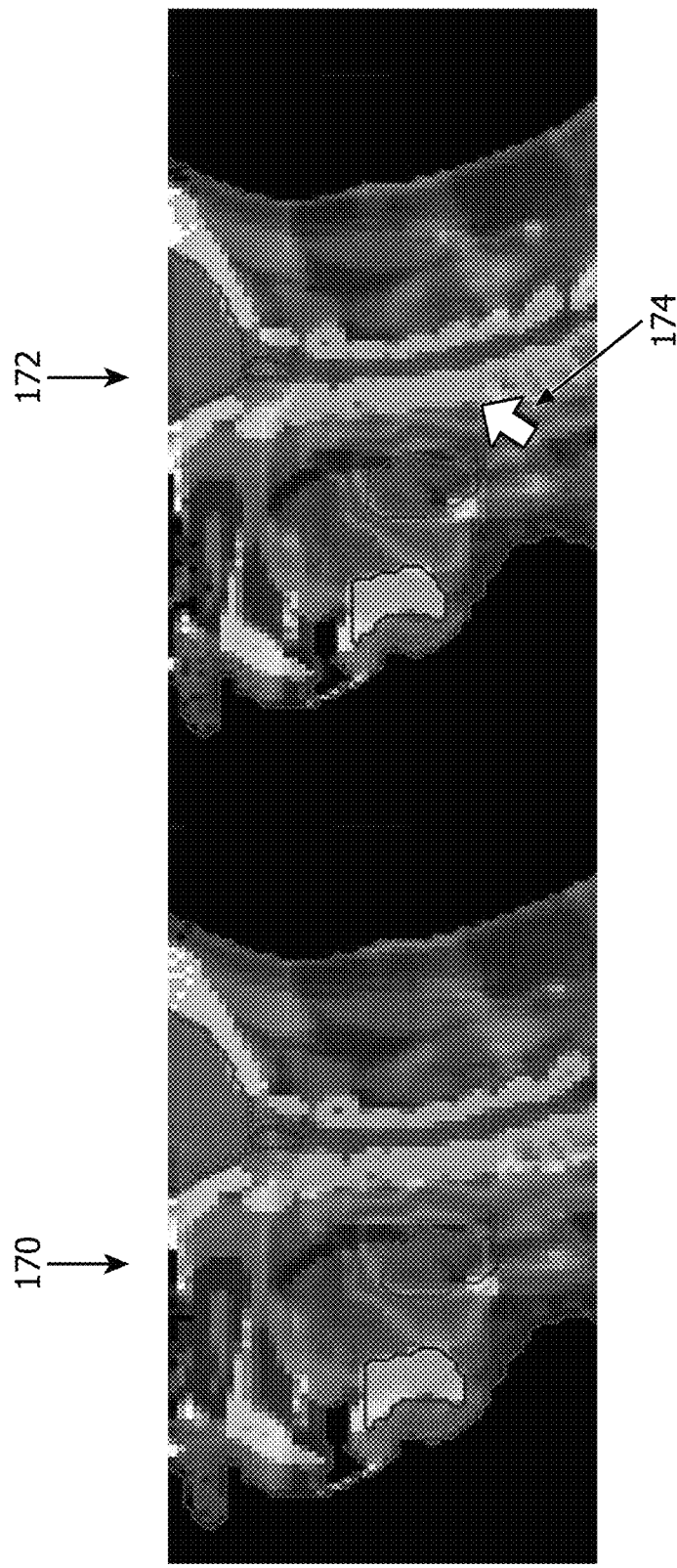

FIG. 8 shows a clinical head-and-neck (HN) case. A left side 150 shows a phantom planning CT and the dose distribution, and a right side 152 shows a shifted re-simulated-CT image. This is for a step-and-shoot IMRT with 9 beams setup, with the angular spacing of the beams being 40°. The voxel grid resolution is (0.2344 cm, 0.2344 cm). A 20% dose objective improvement was achieved using the DPSO method. FIG. 9 shows, on a left side, an initial planning dose objective value 160, with $f$=0.8894, a table 162 with the dose objective values and corresponding optimal δ vectors at different DPSO iterations, and a right side shows a plot 164 of the dose objectives. It is seen that after 2-3 iterations the DSPO iteration converged to a minimum. The objective value factor (with respect to the planning objective value) was reduced from 1.37 to 1.05. FIG. 10 shows, on a left side 170, a re-simulated-CT image and planning dose distribution (i.e., initial shifted resim-CT plan with dose recomputation), and a right side 172 shows an optimal DPSO shifted re-simulated-CT image and corresponding re-computed dose distribution. The arrow 174 indicates the direction of the optimal shift δ vector computed using the DPSO method.

The illustrative examples address the adaptation of a single treatment plan. However, in a variant embodiment, two or more treatment plans can be obtained (e.g. from a non-transitory storage) and the determination of the transformation T (comprising the rigid spatial transform δ) is repeated for the plurality of different treatment plans. In this case, the treatment planning method may further includes selecting one of the corresponding different adapted treatment plans on the basis of the dose objectives (f). In other words, the treatment plan that is selected is the one for which the determined transform T provides an adapted plan with the lowest value for the dose objectives.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A computer program may be stored/distributed on a non-transitory storage medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A non-transitory computer-readable medium storing instructions readable and executable by at least one electronic processor to perform a treatment planning method, the method comprising:
    obtaining a treatment plan generated on the basis of a planning image of a region of a patient body and on the basis of dose objectives with respect to the region of the patient body, the treatment plan corresponding to a dose distribution in the region of the patient body,
    receiving a further image of the region of the patient body,
    determining a transformation for generating an adapted treatment plan by at least one adjustment iteration in which the dose distribution is updated for a rigid spatial transform and the rigid spatial transform is updated on the basis of the dose objectives using a partial derivative of the dose objectives with respect to the rigid spatial transform but not using a partial derivative of the dose objectives with respect to the dose distribution, wherein the transformation comprises the rigid spatial transform updated by the last adjustment iteration; and
    determining an adapted treatment plan for controlling the radiation therapy treatment on the basis of the transformation.

2. The non-transitory computer-readable medium of claim 1, wherein the rigid spatial transform comprises at least one of a rotation or a translation.

3. The non-transitory computer-readable medium of claim 1, wherein the determining of the adapted treatment plan includes determining an adjustment of a patient support or of a position of a radiation therapy device respective to the patient support to implement the transformation.

4. The non-transitory computer-readable medium of claim 1, wherein the determining of the adapted treatment plan does not include determining adjustments to beam parameters of the treatment plan.

5. The non-transitory computer-readable medium of claim 1, wherein the obtaining of the treatment plan and the determining of the transformation is repeated for a plurality of different treatment plans, and the method further includes:
    selecting one of the corresponding different adapted treatment plans on the basis of the dose objectives.

6. The non-transitory computer-readable medium of claim 1, wherein an initial value for the rigid spatial transform is determined using a image registration to spatially register a mask of a tumor and organs at risk (OARs) in the further image and a corresponding mask of the tumor and OARs in the planning image.

7. The non-transitory computer-readable medium of claim 1, wherein the method further includes:
    controlling an imaging device to acquire the further image of the region of the patient body.

8. A treatment planning device comprising:
    at least one electronic processor; and
    a non-transitory computer-readable medium storing instructions readable and executable by the at least one electronic processor to perform a treatment planning method comprising:
        obtaining a treatment plan generated on the basis of a planning image of a region of a patient body and on the basis of dose objectives with respect to the region of the patient body, the treatment plan corresponding to a dose distribution in the region of the patient body;
        receiving a further image of the region of the patient body;
        updating a rigid spatial transform by performing at least one iteration of an update process that does not including computing a partial derivative of the dose objectives with respect to the dose distribution; and
        adapting the treatment plan to generate an adapted treatment plan which includes an adjustment by the updated rigid spatial transform of patient position respective to a radiation treatment device.

9. The treatment planning device of claim 8 wherein the updating includes:

updating the dose distribution for the rigid spatial transform, and updating the rigid spatial transform on the basis of the dose objectives using a partial derivative of the dose objectives with respect to the rigid spatial transform but not using a partial derivative of the dose objectives with respect to the dose distribution.

10. The treatment planning device of claim 8, wherein the rigid spatial transform comprises at least one of one of a rotation or a translation.

11. The treatment planning device of claim 8, wherein the adapting of the treatment plan to generate the adapted treatment plan does not include adjustment of beam parameters of the treatment plan.

12. The treatment planning device of claim 8, wherein the adjustment by the updated rigid spatial transform of the patient position respective to the radiation treatment device includes at least one of:

adjustment of a patient support; or adjustment of a position of the radiation treatment device respective to the patient support.

13. A treatment planning method comprising:

obtaining a treatment plan generated on the basis of a planning image of a region of a patient body and on the basis of dose objectives with respect to the region of the patient body, the treatment plan corresponding to a dose distribution in the region of the patient body, receiving a further image of the region of the patient body, determining a rigid spatial transform for generating at least one of an adapted treatment plan from the treatment plan and an adapted dose distribution from the dose distribution on the basis of the further image and on the basis of the dose objectives using an iterative process that alternates between updating the dose distribution and updating the rigid spatial transform; and adapting the treatment plan to generate an adapted treatment plan which includes an adjustment by the determined rigid spatial transform of patient position respective to a radiation treatment device;

wherein the treatment planning method is performed by at least one electronic processor.

14. The treatment planning method of claim 13 wherein the iterative process includes computing a partial derivative of the dose objectives with respect to the rigid spatial transform.

15. The treatment planning method of claim 13 wherein the iterative process does not include computing a partial derivative of the dose objectives with respect to the dose distribution.

16. The treatment planning method of claim 13, wherein the rigid spatial transform comprises at least one of one of a rotation or a translation.

17. The treatment planning method of claim 13, wherein the adapting of the treatment plan to generate the adapted treatment plan does not include adjustment of beam parameters of the treatment plan.

18. The treatment planning method of claim 13, wherein the obtaining of the treatment plan and the determining of the rigid spatial transform is repeated for a plurality of different treatment plans, and the method further includes:

selecting one of the corresponding different adapted treatment plans on the basis of the dose objectives.

19. The treatment planning method of claim 13, wherein the determining of the rigid spatial transform includes determining an initial value for the rigid spatial transform by spatially registering the further image and the planning image.

20. The treatment planning method of claim 19, wherein the spatial registering employs a deformable image registration procedure.

* * * * *